United States Patent [19]
Beitz et al.

[11] 3,960,493
[45] June 1, 1976

[54] METHOD OF MEASURING THE FAT AND PROTEIN CONTENT IN FLUIDS

[75] Inventors: Donald C. Beitz, Ames; Mitchell E. Phillips, West Des Moines, both of Iowa

[73] Assignee: Iowa State University Research Foundation, Inc., Ames, Iowa

[22] Filed: Nov. 18, 1974

[21] Appl. No.: 524,739

[52] U.S. Cl. ................................ 23/230 B; 23/231; 252/408
[51] Int. Cl.² ................. G01N 31/02; G01N 33/06; G01N 33/16
[58] Field of Search ............ 23/231, 230 B; 252/408

[56] References Cited
UNITED STATES PATENTS

| | | | |
|---|---|---|---|
| 3,746,511 | 7/1973 | Stookey et al. | 23/231 |
| 3,841,834 | 10/1974 | Gandhi et al. | 23/231 |
| 3,884,638 | 5/1975 | Dixon et al. | 23/230 B |

OTHER PUBLICATIONS

Analytical Abstracts, vol. 20, Abstract No. 2687, 1971.

Helman et al., "Evaluation of Light Scattering Index (Neplelometry) for Assessing Serum Triglycerides and Lipoprotein phenotypes," copyright 1970 by the American Assoc. of Clin. Chemists.

*Primary Examiner*—Morris O. Wolk
*Assistant Examiner*—Barry I. Hollander
*Attorney, Agent, or Firm*—Wolfe, Hubbard, Leydig, Voit & Osann, Ltd.

[57] ABSTRACT

Nephelometric method for sequential determination of protein and fat in a milk sample. Distinct reagent solutions are added to a milk sample which are effective to sequentially form colloidal dispersions of protein and fat, respectively, while effecting solubilization of the other. Nephelometric readings are taken after the addition of each reagent solution and, as a result thereof, the measured turbidity is a direct function of the particular solid dispersed.

10 Claims, No Drawings

METHOD OF MEASURING THE FAT AND PROTEIN CONTENT IN FLUIDS

This invention relates to the analysis of fluids containing fat and protein and, more particularly, to the quantitative determination of these substance in bovine milk.

Bovine milk is recognized as a good source of high quality protein, minerals and fat for the world food supply. As a result, emphasis is currently being placed on upgrading the nutritive qualities of milk. Important in accomplishing this is the ability to reliably determine the content of fat and protein in milk samples from various breeds, and also from variations in the presence of these substances within a given breed occasioned by differences in feeding, herd management and the like.

Complex and generally expensive procedures and equipment are available for the rapid determination of milk fat and protein. The problem has resided in providing an inexpensive and easy method which is adaptable for fast, small scale use. A nephelometric procedure, which involves quantitatively ascertaining solids content in a fluid by measurement of turbidity, would have the aforementioned advantages as to simplicity, rapidity and small scale. The principal problem heretofore encountered in the effective implementation of a nephelometric procedure has resided in being able to independently measure both fat and protein content in a single milk sample without the necessity for laborious prior extraction and separation of these constituents.

Accordingly, it is a principal object of the present invention to provide a nephelometric procedure for the quantitative determination of fat and protein content of milk. A complementary objective resides in providing an inexpensive, easy and fast method for independently ascertaining fat and protein content in milk which requires only a small amount of sample.

A further object resides in providing a procedure for the determination of fat and protein content in milk in which a single sample can be used and wherein prior separation and isolation between fat and protein is not needed.

Yet another object resides in providing a nephelometric procedure having the foregoing attributes which is applicable in reliably determining the fat and protein content from milk samples obtained from different breeds of cattle or containing different concentrations of protein. Related to this object, an added objective resides in providing a nephelometric procedure wherein interference from other milk constituents is avoided.

Still a further object of this invention is to provide reagent solutions useful in a nephelometric procedure of the above character which can be used to selectively and sequentially solubilize one of the constituents to be measured while effecting a stable colloidal dispersion of the other. Related to the foregoing is the added object of providing reagent solutions which serve to enhance and stabilize colloidal dispersability of the insoluble constituent and thereby permit accurate nephelometric measurements which are substantially a linear function of the concentration of the dispersed constituent.

A further and more particular object of this invention is to provide a method adaptable to on-the-farm testing of milk from individual cows or groups of cows to thereby permit use by dairy herd improvement associations in establishing fat and protein production records for each individual cow; thus providing a testing basis so that the payment to dairymen for milk on the basis of protein concentration can be implemented. Such a method will be of great value to the seller and purchaser of milk through a knowledge of the protein content of that milk.

Other objects and advantages of the present invention will become apparent upon reference to the following detailed description of the invention. And, while the invention is described in connection with certain preferred embodiments and procedures, it is to be understood that the invention is not to be limited to those embodiments and procedures. On the contrary, all alternatives, modifications, and equivalents as can be included within the scope and spirit of the invention defined in the appended claims are intended to be covered.

Briefly, the nephelometric procedure illustrated herein involves adding distinct reagent solutions to a single milk sample which are effective to sequentially form colloidal dispersions consisting essentially of protein and fat, respectively. Nephelometric readings are taken after the addition of each reagent solution and, consequently, the measured turbidity is a direct function of the particular solids dispersed. As should be apparent, the particular reagent solutions used to disperse protein or fat (hereinafter referred to as the protein reagent solution and the fat reagent solution) must be selected so as to effect maximum colloidal dispersion of the respective constituent while assuring that the other constituent is substantially completely soluble.

Turning to the protein reagent solution, this is anhydrous and preferably consists essentially of an acetic anhydride, para-toluene sulfonic acid and acetic acid. It is believed that the anhydride is effective to reversibly denature the protein (both whey and casein) present in the milk sample and thereby cause protein precipitation.

The presence of para-toluene sulfonic acid, which is a strong acid, is considered necessary in order to prevent agglomeration of the protein precipitate to yield a desirable colloidal dispersion. It is also believed that the presence of this acid increases the rate of acetic anhydride to acetic acid reaction, thus making the mixture anhydrous more rapidly. Moreover, by being a stronger acid than acetic anhydride, it is postulated that the toluene sulfonic acid sufficiently raises the positive zeta potential on the surface of the precipitated protein so as to cause the precipitate to disperse.

As to the acetic acid present in the solution, this functions as the principal fat solubilizing constituent While the fat content of bovine milk is soluble in acetic anhydride, with or without para-toluene sulfonic acid, the presence of acetic acid in the protein reagent solution is nevertheless desirable. Acetic acid is useful in permitting easy adjustment of anhydride concentration so as to effect rapid formation of a stable protein dispersion and also aids in achieving subsequent dissolution of protein on addition of the fat reagent solution.

Referring still to the protein reagent solution, the proportional amounts of the ingredients contained therein are important. To this end, it has been found that the concentration of para-toluene sulfonic acid in the solution should be less than about 1 gram per one hundred milliliters of solution and, preferably, is between about 0.25 and 0.75 grams. While sufficient sulfonic acid must be present in order to effect desirable protein dispersion, re-dissolution is effected as the amount of this ingredient is increased. Also, so long as the concentration is maintained as above expressed, the presence of the sulfonic acid appears to have no effect on the subsequent determination for fat content.

Concerning the amount of anhydride employed, it is preferred that it be about 5 to 20 percent, by volume, with the balance being acetic acid. However, since precipitate formation is quite sensitive to the presence of water in the milk sample, an anhydride concentration of at least about 10 volume percent and preferably at least 15 percent is most useful. In addition, with higher acetic anhydride concentrations, e.g. about 15 volume percent, rapid precipitation is effected and the colloidal dispersion so formed has enhanced stability. That acetic acid is the principal constituent of the protein solution permits ready adjustment of anhydride content therein to achieve the foregoing attributes.

The amount of protein reagent solution added to the milk sample must be sufficient to precipitate protein and dissolve fat. Based on 0.05 ml of milk sample, the addition of about 3–7 ml of reagent solution can be used with about 4–6 ml being preferred.

Turning now to the fat reagent solution, it will be appreciated that this solution is added to the colloidal dispersion formed by adding the protein reagent solution to the milk sample. Basically, the fat reagent solution is water, the addition of which precipitates fat colloids due to fat insolubility in aqueous solutions and to the specific gravity difference between the aqueous acidic solution and the milk fats. Also, the water effectively dissolves the reversibly denatured protein in dispersion. So as to effectively accomplish its stated objectives, water in added in an amount which is at least about one-third, and preferably at least about one-half, of the amount of protein reagent solution employed.

While the addition of water as the fat reagent solution is effective to precipitate fat and solubilize protein, in order to stabilize the colloidal fat dispersion, it is desirable to include in the fat reagent solution a small amount of a non-ionic surfactant which is soluble in acid solutions. In this respect, useful fat reagent solutions contain up to about 10 grams of surfactant per 100 milliliters of solution. A small amount of the surfactant can also be present in the protein solution.

As to useful non-ionic surfactants, polyethylene oxide condensates are most useful and particularly those which are prepared by condensation of polyoxyethylene glycols and alkyl phenols. Of these, those prepared with dialkyl phenols such as are sold by GAF under the trademark IGEPAL DM are especially useful.

Customary nephelometric manipulative procedures can be used in accomplishing the present invention using commercially available turbidimeters, standards and the like. A particularly preferred instrument is Model No. 2424 supplied by Hach Chemical Company. As to standards, a Formazin standard which is prepared by the reaction of hydrazine sulfate and hexymethylenetetramine is preferred. Also, in accordance with customary techniques, it is desirable that prior to analysis, the whole milk sample be appropriately homogenized. Such can be accomplished by simply mixing the sample until it is homogeneous at about 20°C., or, if necessary, warming the sample to 38°C. and then cooling the sample to about 20° C. before testing.

The following example illustrates the present invention.

PREPARATION OF PROTEIN REAGENT SOLUTION 0.50 grams of para-toluene sulfonic acid was added to a 150 ml beaker followed by the addition of 15.75 ml of acetic anhydride. The mixture was stirred by swirling and 84.25 ml of glacial acetic acid was added to the beaker and the reagent solution mixed by pouring back and forth several times into a container. The resulting solution was stored in a closed container at room temperature and is stable for at least several weeks.

PREPARATION OF FAT REAGENT SOLUTION 15 ml of non-ionic water was heated to boiling and 5.0 grams of IGEPAL DM-970 surfactant was added into a 100 ml flask and the hot water added in the amount necessary to dissolve the surfactant. Thereafter the solution was cooled to room temperature and then diluted to volume with deionized water.

PREPARATION OF FORMAZIN STANDARD 5.0 grams of reagent grade hydrazine sulphate was added to a one liter flask containing about 400 ml of distilled water. 50.0 grams of pure hexamethylenetetramine was dissolved in a separate flask containing 400 ml distilled water. This solution was then quantitatively transferred to the one liter flask and the resulting solution mixed followed by the addition of distilled water to give 1000 ml. Reaction was then allowed to proceed at 20°–22° C. for forty-eight hours. The resulting formazin standard solution was equal to 4000 formazin turbidity units (FTU).

NEPHELOMETRIC PROCEDURE

A Hach Chemical Company clinical turbidimeter (NO. 2424) with the cell adapter in place was turned on and allowed to warm up for about twelve hours. 0.05 ml of a milk sample was pipetted into a clean 13 × 100 mm scratch free test tube and 5.0 ml of protein reagent solution added to the tube. The tube was stoppered with an acid resistant clean rubber stopper and mixed by inversion three or four times and the stopper removed. The turbidimeter was set at range 1 and the zero and standardization controls turned to full right. The instrument was then zeroed with distilled water and a sample of the Formazin standard, diluted to 100 FTU, placed in the cell adapter and the meter reading adjusted to 100 on scale. The milk sample containing the protein reagent solution, after having been permitted to stand at least fifty minutes at room temperature, is then inserted into the cell adapter, covered with a light shield and the meter reading recorded. The percent protein in the milk sample is then calculated using the following formula:

% Protein=(Scale reading + 6.7)/(19.3)

The sample is then removed from the instrument and 2.5 ml of the fat reagent solution is added. So that equal colloid formation is effected, the tube is quickly stoppered and immediately inverted and then allowed to stand at room temperature for about 10 to 30 minutes. For fat determination, the turbidimeter is set at range 10 with a 150 FTU Formazin standard used with a meter reading of 50 on scale. Percent fat in the sample is calculated using the following formula:

$$\% \text{ Fat} = (\text{Scale reading} - 2.2)/(14.4)$$

A number of samples of bovine milk were analyzed for fat and protein using the above described procedure and the results thereof compared with results obtained using the customary Babcock and Kjeldahl methods for determining fat and protein. Good correlation between the methods was obtained for various milk samples differing in breed and the like. Thus the present procedure is insensitive to such variations and also the presence of other milk constituents such as lactose. Because the illustrated technique is a micromethod, it should be apparent that it is adaptable to various types of biological studies where determination of fat and protein are desired. Thus, in addition to the analysis of milk, the technique is considered to be useful for protein and fat determination in other kinds of biological fluids, such as lymph, blood and spinal fluid. It is also expected to be useful in the analysis of solubilizeable foods.

Accordingly, it can be seen that the present invention fully satisfies the aims and objectives heretofore identified. The illustrated method is fast and accurate and involves the use of only small samples. In addition, because the fat and protein precipitates formed are repeatable, and directly related to a Formazin standard, precalibrated meter scales on a nephelometer can be constructed and direct measurements made.

We claim as follows:

1. A nephelometric method for the sequential determination of protein and fat in a biological fluid sample containing protein and fat comprising the steps of (1) adding to the sample a first reagent solution which is substantially anhydrous and is effective to dissolve the fat content of the sample and to substantially denature the protein therein to thereby provide a colloid protein dispersion, (2) taking a nephelometric reading of the colloidally dispersed protein in the sample, (3) adding to the sample prepared in step (1) a second solution comprised predominantly of water which precipitates the fat in the sample so as to form a colloidal fat dispersion and which dissolves the protein, and (4) taking a nephelometric reading of the colloidally dispersed fat.

2. The nephelometric method of claim 1 wherein the second reagent solution is water and a small amount of a non-ionic surfactant.

3. The nephelometric method of claim 2 wherein the sample is milk and the first reagent solution consists essentially of acetic anhydride, para-toluene sulfonic acid and acetic acid.

4. The nephelometric method of claim 3 wherein the first reagent solution contains less than about 1 gram para-toluene sulfonic acid per 100 milliliters of solution and wherein acetic anhydride is present in an amount of about 5 to 20 percent by volume, the balance of the solution being acetic acid.

5. The nephelometric method of claim 4 wherein the first reagent solution contains between about 0.25 and 0.75 grams para-toluene sulfonic acid per 100 milliliters of solution and wherein about 15 to 20 percent by volume of the solution is acetic anhydride.

6. The nephelometric method of claim 5 wherein, per 0.05 ml of sample, about 3 – 7 ml of the first reagent solution are used and wherein the second reagent solution is added in an amount which is at least about one-third of the amount of the first reagent solution employed.

7. The nephelometric method of claim 5 wherein, per 0.05 ml of sample, about 4 – 6 ml of the first reagent solution are used and wherein the second reagent solution is added in an amount which is at least about one-half of the amount of the first reagent solution employed.

8. A reagent solution, useful for the nephelometric determination of protein in a milk sample, said solution containing para-toluene sulfonic acid, acetic anhydride, and acetic acid, the para-toluene sulfonic acid being present in an amount of less than about 1 gram per 100 milliliters of solution and the acetic anhydride being present in about 5–20 percent by volume, the balance of the solution consisting essentially of acetic acid.

9. The reagent solution of claim 8 wherein the para-toluene sulfonic acid is present in an amount of between 0.25 and 0.75 grams per 100 milliliters of solution and the acetic anhydride is present in an amount of about ten to twenty percent by volume.

10. The reagent solution of claim 9 wherein 0.5 gram of para-toluene sulfonic acid is present per 100 milliliters of solution and wherein acetic anhydride is present in about 15 per cent by volume.

* * * * *